United States Patent [19]

McGregor

[11] Patent Number: 5,002,565

[45] Date of Patent: Mar. 26, 1991

[54] SURGICAL NEEDLE CONFIGURATION WITH STAR SHAPED CROSS-SECTION

[75] Inventor: Walter McGregor, Flemington, N.J.

[73] Assignee: Ethicon, Inc., Somerville, N.J.

[21] Appl. No.: 423,828

[22] Filed: Oct. 19, 1989

[51] Int. Cl.[5] .............................................. A61B 17/06
[52] U.S. Cl. .................................................... 606/223
[58] Field of Search .............. 606/181, 182, 183, 185, 606/186, 187, 222, 223, 148; 223/102, 103, 104

[56] References Cited

U.S. PATENT DOCUMENTS

| 461,602 | 10/1891 | Boult | 223/102 |
|---|---|---|---|
| 3,038,475 | 6/1962 | Orcutt | 128/339 |
| 4,513,747 | 4/1985 | Smith | 128/339 |
| 4,524,771 | 6/1985 | McGregor et al. | 128/339 |
| 4,660,559 | 4/1987 | McGregor et al. | 128/339 |
| 4,799,484 | 1/1989 | Smith et al. | 128/339 |
| 4,932,961 | 6/1990 | Wong et al. | 606/223 |

*Primary Examiner*—Michael H. Thaler
*Attorney, Agent, or Firm*—Paul A. Coletti

[57] ABSTRACT

A needle having ten edges, forming a star-shaped cross-section. The needle also presents a tapered end. With reduced cross-sectional area, the improved needle results in easier tissue penetration, better wound opening area performance, and minimized tissue distortion. In an alternate embodiment, wound opening is further reduced by creating an eight-sided, star-shaped needle cross-section.

11 Claims, 2 Drawing Sheets

SURGICAL NEEDLE CONFIGURATION WITH STAR SHAPED CROSS-SECTION

FIELD OF THE INVENTION

The present invention relates generally to improved surgical needles. More specifically, the present invention relates to surgical needles which have improved sharpness and reduced penetration resistance between needle and tissue during surgery. Most specifically, the present invention relates to a surgical needle whereby the wound opening area is reduced in order to better perform sensitive surgeries by minimizing tissue distortion and improving tissue apposition.

BACKGROUND OF THE INVENTION

The performance criteria of surgical needles can be measured in three interrelated ways. First, needle sharpness is necessary to reduce penetration resistance between needle and tissue. Greater sharpness lessens the external force required to embed the needle into tissue during surgery. Second, it is desirable to improve the needle cross-section so that the tissue opening, more commonly referred to as the wound opening site, is also reduced. As suspected, with improved penetration, the wound opening is also reduced. Third, when wound opening size is reduced, this will generally minimize the amount of tissue distortion during penetration of the needle.

With improved penetration, reduced wound opening and minimized tissue distortion, tissue apposition is generally improved. As a result, finer and more approximate surgery is possible. Thus, with improved needle sharpness, it is increasingly possible to perform more specialized surgery, especially in such highly refined areas as ophthalmology, microsurgery or plastic surgery.

Generally, it has been found that the optimal needle point must have a sharply tapered end, as well as a reduced cross-section. With a sharply tapered end, it is possible to achieve penetration without maximum tissue distortion. The reduced cross-section in this case will also reduce the wound opening area. It has been found that needles triangular in cross-section have performed quite well in conjunction with tapered ends.

Nevertheless, even these triangular needles require refining in order to improve the previously stated needle sharpness criteria. That is, none of the generally triangular needles have acceptably improved all the criteria in order to configure an optimal needle. Triangular shaped cross-section needles usually sacrifice one criterion for an increased benefit in another criterion.

What is needed, therefore, is a needle with improved sharpness which also reduces penetration resistance, as well as reducing wound opening area and minimizing tissue distortion. With this optimized needle cross-section, improved tissue apposition is possible, and highly refined surgery is generally more likely.

SUMMARY OF THE INVENTION

Accordingly, it is an object of the present invention to provide a needle with a tapered cutting edge having a reduced cross-sectional area for improved penetration.

It is further an object of the present invention to provide a surgical needle with a tapered cutting edge having an easy to form cutting edge which results in improved penetration and smaller wound opening.

Finally, it is an object of the present invention to provide a needle which has edges containing surfaces which can be polished to improve their sharpness.

These and other objects of the present invention are accomplished in a surgical needle having a tapered cutting edge and containing a star-shaped cross section. The cross section is generally comprised of flat upper surface which forms a first side of the needle. The first side contains two ends and from each first side end there extends a diverging angular surface. Each diverging angular surface contains an end from which extends a further diverging angular surface. Thus, on one half of a needle cross-section, there are five separate diverging surfaces. The entire needle is symetrically shaped so that the five surfaces forming the upper side of the needle are matched by a similar five surfaces which form the lower side of the needle. The divergent fourth and fifth sides of the upper half meet a lower pair of diverging fourth and fifth sides at an acute angle. This acute angle and the taper in the needle itself creates a reduced cross-section and refined point for easier penetration and smaller wound opening.

In an alternate embodiment, the flat upper and lower surfaces are removed, resulting in an eight-sided star-shaped cross section. Again, because the diverging angular surfaces of the upper and lower sections of the needle meet at an acute angle, the result is a sharper surface; this needle embodiment also optimizes penetration, and reduces wound opening size.

This present invention will more readily be understood by the accompanying description of the drawings and the detailed description of the invention, in which:

DETAILED DESCRIPTION OF THE DRAWINGS

DETAILED DESCRIPTION OF THE INVENTION

Figure 1:
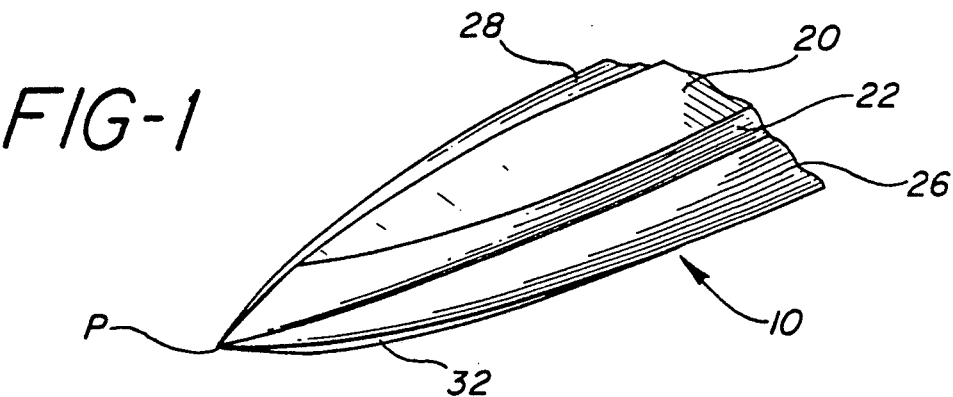
FIG. 1 is a perspective view of a surgical needle of the present invention.
Figure 2:
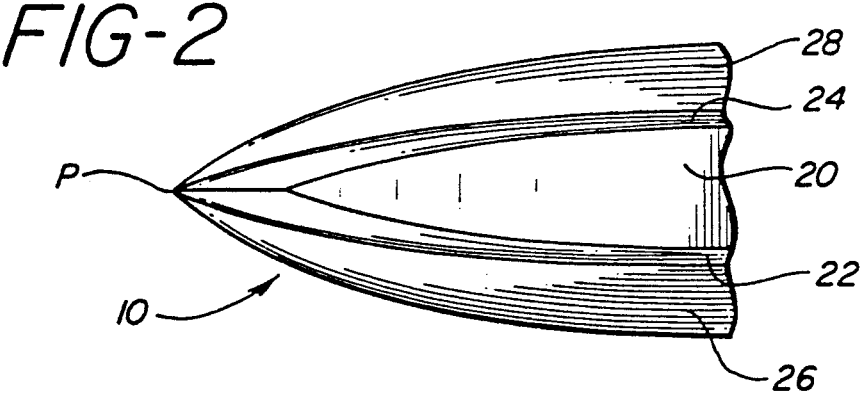
FIG. 2 is a top view of a surgical needle of the present invention.
Figure 3:
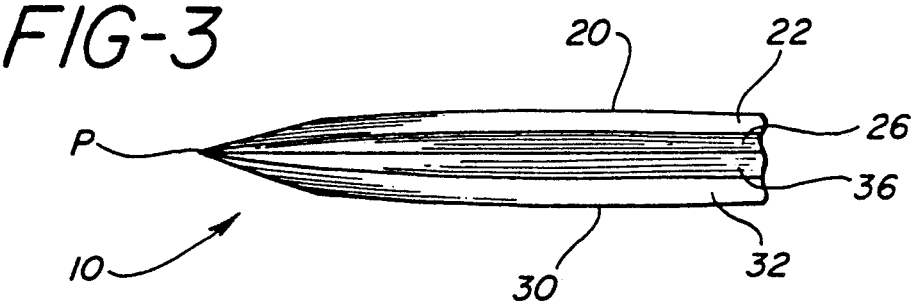
FIG. 3 is a side view of a surgical needle of the present invention.
Figure 4:
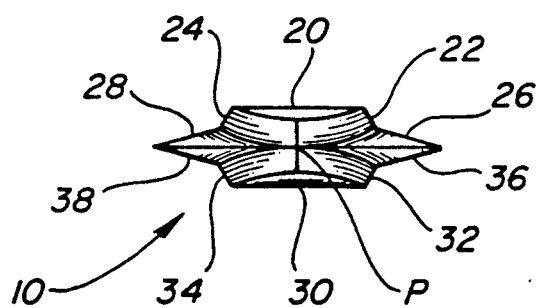
FIG. 4 is a end view of a surgical needle of the present invention.
Figure 5:
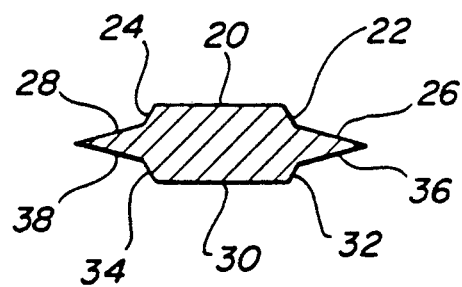
FIG. 5 is a cross-sectional of view taken along lines 5—5 of FIG. 2.

As can be seen of FIGS. 1-5 the improved needle configuration of the present invention comprises needle 10. This needle contains a flat upper surface 20 and a flat lower surface 30. Extending from the ends of the flat upper surface 20 are a pair of first edges 22, 24. These first edges 22, 24 extend angularly away from the flat upper surface 20. At the end of the pair first edges 22, 24 extend a pair of second edges 26, 28. These second edges 26, 28 extend angularly away from the pair of first edges 22, 24.

Similarly, the needle 10 also contains a flat lower surface 30 generally parallel to flat upper surface 20. Extending angularly from the flat lower surface 30 are a pair of third edges 32, 34 which correspond to the pair of first edges 22, 24. Extending from the pair of third edges 32, 34 are a pair of fourth edges 36, 38. These edges 36, 38 correspond symmetrically to the pair of second edges 26, 28.

Thus, the upper surface combination 26-22-20-24-28 is symetrical to the lower surface combination 36-32-30-34-38. The pair of second edges 26, 28 meet the pair of fourth edges 36, 38 at acute angles. All ten surfaces taper to a point p at the edge of the needle.

Figure 6:
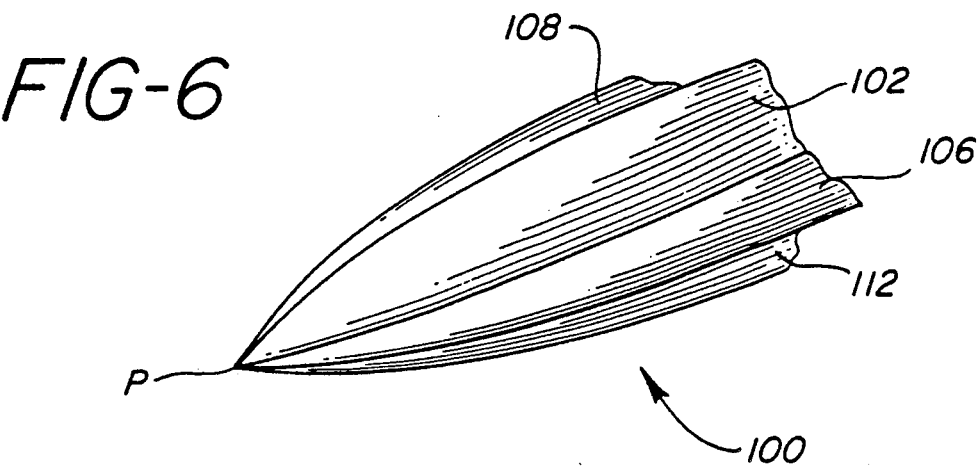
FIG. 6 is a perspective view of a needle of an alternate embodiment of the present invention.
Figure 7:
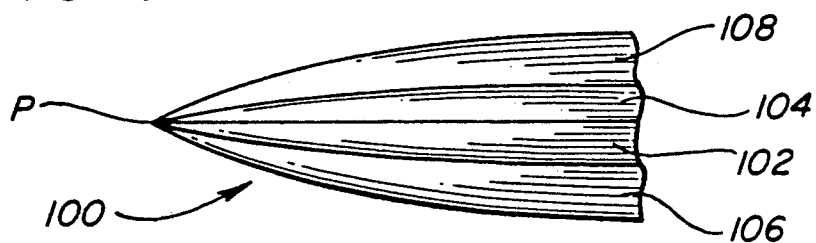
FIG. 7 is a top view of an alternate embodiment of present invention.
Figure 8:
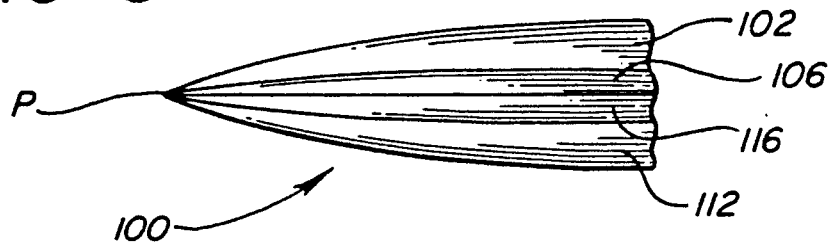
FIG. 8 is a side view of an alternate embodiment of the present invention.
Figure 9:
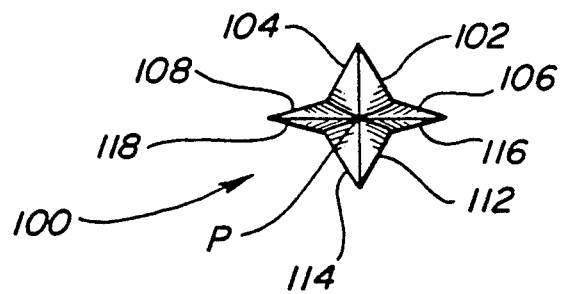
FIG. 9 is an end view of an alternate embodiment of the present invention.
Figure 10:
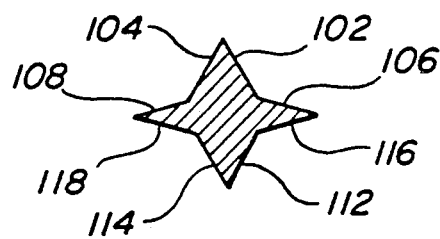
FIG. 10 is a cross sectional view of an alternate embodiment of the present invention as taken along lines 10—10 of FIG. 7.

Alternately, as seen in FIGS. 6-10 there is presented a star-shaped needle 100. This needle 100 cross-section does not contain the upper and lower surfaces 20,30 shown in FIGS. 1-5 of needle 10. Thus, needle 100 contains a pair of first edges 102, 104 which extend angularly from one another. These first edges 102, 104 terminate in a pair of second edges 106, 108. Symmetrically corresponding to the pair of first edges 102, 104 are a pair of third edges 112, 114 which in turn diverge away from one another. A pair of fourth edges 116, 118 correspond symmetrically to the pair of second edges 106, 108 and diverge further away from the pair of third edges 112, 114. The pair of fourth edges 116, 118 joins the pair of second edges 106, 108 at an acute angle. Similar to needle 10, the needle 100 ends in tapered point p so that the entire needle tapers, as can be seen in FIGS. 6, 7, and 8.

The exact size and curvature of the needle of the present invention is, of course, a matter of choice. Generally, both needles 10, 100 will be formed from a strengthened alloy and have a thickness (diameter) anywhere from 0.004 inches to 0.061 inches. The radius of curvature of the needle, if any, will generally be anywhere from 0.050 inches to about 6 inches. The length of the arc of the needles 10, 100 will depend on choice, from ¼ to ⅝ of a circle. By choice, naturally, some needles will remain straight. In all cases, the points P should be as sharp as possible, generally between 1° and 40°.

As needle 10 is configured, it is desired to have the pair of first edges 22, 24 diverge from the upper surface 20 at the same rate by which the pair of third edges 32,34 diverge from the lower surface 30. Also, by causing these included angles to be larger, the needle itself is "flatter", presenting a reduced surface area for wound penetration. Thus, while theoretically, the included angle between for example, sides 20 and 22 could be anywhere from 90° to 180°, generally about 100° to about 150° is preferred. It has been found that an included angle of about 120° is most optimal for needle sharpness. Of course, the angle between surfaces 20,22 should be identical (within ±3°) of the included angles between surfaces 20, 24 and 30,32 and 30,34.

Again, because it is desired to create a "shallow" needle 10 with sharp side piercing edges, the included angle between surfaces 22, 26 and 24, 28 and 32, 36 and 34, 38 should allow the overall configuration of the needle cross-section to present a "hollow" between, for instance, side 20 and the sharp side created at the intersection of edges 28, 38. Thus, the included angles for these four "hollows" should be greater than 180°, with anywhere from about 200° to about 240° being preferred. Optimally, about 210° has been found to produce the most efficient penetration while reducing wound area.

Completing the configuration of needle 10, sharpened edges created at 26, 36 and 28, 38 which should allow the needle to obtain efficient overall piercing. Thus, these edges should be maintained between 10° and 40°, with about 20° or less found to be most optimal, and can be accomplished using known polishing techniques.

Correspondingly, needle 100 should also maintain the desired overall sharpness for penetration, while creating "hollowed" edges for reduced wound area. Therefore the union of sides 106, 116 and 108, 118 correspond to the sharpened edge on needle 10 created by sides 26, 36 and 28, 38. The included angle should be between 10° and 40°, with about 20° or less found to be most efficient.

The edges created by sides 102, 104 and 112, 114 also correspond to needle 10, with upper and lower sides 20, 30 removed. Thus, the included angles between sides 102, 104 and 112, 114 are between about 20° and 120°, depending on the desired depth of the needle edge, correspondingly, about 40° is the most preferred angle.

Finally, the included angles between sides 102, 106 and 104, 108 and 112, 116 and 114, 118 correspond to the "hollow" created in needle 10. Therefore, these included angles should also range from about 200° to about 240°, with about 210° being preferred. Also, in the embodiments described above, the sides in cross-section are straight as shown in FIGS. 4, 5, 9 and 10.

Thus, with the improved needle edges in the star-shaped present design, the objectives for an improved needle are accomplished. Tissue penetration is performed more readily. Wound opening area is reduced, due to the cross-section of the needle, which contains a reduced cross-sectional area, and the sharper edges contained on both embodiments of the needle. Finally, tissue distortion is minimized, and improved tissue apposition is available.

While the present invention has been described in conjunction with a particular preferred embodiment, it should be understood that the invention should be determined from the following claims in their equivalents in which:

What is claimed is:

1. A surgical needle having a tapered cutting edge with a star-shaped cross-section, said cross-section comprising:
   a pair of straight first sides diverging from each other;
   a pair of straight second sides, each of said second sides attached to a said first side along an angled intersection, each of said second sides diverging from each other and said first sides;
   a pair of straight third sides corresponding to said first sides, said third sides diverging from each other;
   a pair of said straight fourth sides corresponding to said second sides, each said fourth side attached to a said third side along an angled intersection, each of said fourth sides diverging from each other and said third sides; and
   each of said fourth sides attached to a second side along an angled intersection.

2. The needle of claim 1 wherein the intersecting angles between each said second side and said fourth side are between 10° and 40°.

3. The needle of claim 1 wherein the intersecting angles between each said first side and said second side is equal to the intersecting angles between each said third side and said fourth side, all said angles between 200° and 240°.

4. The needle of claim 3 wherein the intersecting angles between said second side and said fourth side are between 10° and 40°.

5. The needles of claim 4 wherein the tapered end of said needle has an angular point, said angle between 1° and 40°.

6. The needle of claim 1 wherein said pair of first sides is connected by an upper, generally flat needle surface and said pair of third sides is connected by a lower, generally flat needle surface, said upper and lower surfaces generally parallel to one another.

7. The needle of claim 6 wherein said intersection angles between each said second side and said fourth side are between 10° and 40°.

8. The needle of claim 6 wherein the intersecting angles between each said first side and said second side is equal to the intersecting angles between each said third side and said fourth side, all said angles between 200° and 240°.

9. The needle of claim 8 wherein the intersecting angles between said second side and said fourth side are between 10° and 40°.

10. The needle of claim 9 wherein the included intersecting angles between each said first side and said upper surface is equal to the included intersecting angles between each said third side and said lower surface, each said included intersecting angle ranging from about 100° to about 150°.

11. The needle of claim 10 wherein the tapered end of said needle has an angular point, said angle between 1° and 40°.

* * * * *